(12) United States Patent
Hopper

(10) Patent No.: US 8,523,896 B2
(45) Date of Patent: Sep. 3, 2013

(54) DYNAMIC NASAL MOLDING METHOD

(75) Inventor: Richard A. Hopper, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 66 days.

(21) Appl. No.: 13/426,161

(22) Filed: Mar. 21, 2012

(65) Prior Publication Data

US 2012/0191186 A1  Jul. 26, 2012

Related U.S. Application Data

(62) Division of application No. 12/288,048, filed on Oct. 16, 2008, now Pat. No. 8,323,308.

(60) Provisional application No. 60/999,252, filed on Oct. 16, 2007.

(51) Int. Cl.
*A61M 29/00* (2006.01)

(52) U.S. Cl.
USPC ........................................... 606/196

(58) Field of Classification Search
USPC ............. 606/191, 199, 204.45, 196, 201; 128/848, 858
See application file for complete search history.

(56) References Cited

U.S. PATENT DOCUMENTS

2005/0203534 A1  9/2005  Mommaerts
2007/0219575 A1  9/2007  Mejia

OTHER PUBLICATIONS

Grayson et al., Presurgical nasoalveolar Orthopedic Molding in Primary Correction of the Nose, Lip, and Alveolus of Infants Born with Unilateral and Bilateral Clefts, Cleft Palate Craniofacial Journal, May 2001, vol. 38, No. 3, US.

*Primary Examiner* — Gary Jackson
*Assistant Examiner* — Christopher Schubert
(74) *Attorney, Agent, or Firm* — Thomas C. Saitta

(57) ABSTRACT

A dynamic nasal molding device for presurgical molding of cleft lip deformities, the device having a pair of rotation assemblies each having an internal shaping member for insertion in a nostril and an external shaping member to be positioned external to the nostril, wherein the internal and external shaping members are progressively pivoted about the rotation assemblies, while simultaneously the separation distance between the rotation assemblies is decreased, to mold the nasal anatomy into the desired shape.

19 Claims, 4 Drawing Sheets

DYNAMIC NASAL MOLDING METHOD

This application is a divisional application of U.S. Non-provisional patent application Ser. No. 12/288,048, filed Oct. 16, 2008 now U.S. Pat. No. 8,323,308, claiming the benefit of U.S. Provisional Patent Application Ser. No. 60/999,252, with filing date of Oct. 16, 2007, the disclosure of which is incorporated herein by reference.

BACKGROUND OF THE INVENTION

This invention relates generally to the field of orthopedic appliances used to presurgically ameliorate congenital cleft lip deformities in infants by the application of direct controlled molding forces, such appliances often referred to as nasoalveolar molding (NAM) appliances, as well as to methods of correcting cleft lips using such NAM appliances.

A key component of the cleft lip deformity is nasal asymmetry and abnormal form. Current surgical techniques can achieve limited correction. Pre-surgical nasal molding has become popular in large cleft centers in an attempt to minimize the nasal deformity prior to surgery. Unlike adult cartilage, the nasal cartilages of an infant are responsive to external molding pressures and will permanently change shape. The current state of the art pre-surgical treatment (nasoalveolar molding) is limited to linear molding changes on the nostrils, and requires an oral splint for stabilization of the nasal molding component. The traditional NAM treatment protocol requires weekly visits to the orthodontist over the first three months of life of the infant for progressive manual adjustment of the NAM device to alter the molding forces on the infant's alveolus and nasal anatomy. The traditional NAM device relies on taping across the base of the nose to achieve medial movement of the lateral crura and alar bases, and a separate pressure post based on an acrylic oral splint to fit inside the nostril and lift the nasal tip. Limitations of this existing technique are that the taping force is extremely variable in achieving the desired result, can distort the upper lip, and since the upward force is more powerful than the taping, an enlarged, iatrogenic triangulated nostril deformity can result.

It is an object of this invention to provide a device and a method that addresses the problems encountered in the known devices and methods for presurgical molding and shaping of anatomical members distorted or improperly formed due to the presence of a cleft lip. It is a further object to provide a dynamic nasal molding device that creates a three-dimensional rotational change in nasal morphology in preparation for corrective surgery, which device is self-retaining and self-supporting due to opposing tension across the nose, to rotate the lateral crura and alar crease of the lower lateral cartilages of the nose medially and superiorly, while simultaneously elevating the genu and soft triangle of the nasal tip superiorly, with the simultaneous, coordinated and progressive rotational molding of the nostril width and height precluding nasal aperture distortion or enlargement. It is a further object to provide such a device that can be adjusted quickly and easily during the molding process even by non-medical personnel that are properly instructed, such that frequent visits to medical facilities are not required.

SUMMARY OF THE INVENTION

A dynamic nasal molding device is presented that is an adjustable orthopedic appliance adapted for shaping and molding the cartilage, tissues, etc. of the nose, upper mouth, gums and upper lip of infants having unilateral or bilateral cleft lips in order to promote symmetry and proper morphology of these anatomical features prior to the corrective surgical procedures used to close the cleft. The dynamic nasal molding device is self-supporting and self-retaining on the patient. The dynamic nasal molding device is easily sized and oriented relative to each patient, and incremental adjustment of the device during the corrective process is easily accomplished.

The dynamic nasal molding device comprises a main frame assembly, a pair of rotation assemblies connected to the frame assembly, a pair of intra-nasal extensions or internal shaping members and a pair of extra-nasal extensions of external shaping members connected to the rotation assemblies, with means for adjusting the main assembly to adjust the lateral spread or separation distance between the rotation assemblies, means for repositioning the internal shaping members and external shaping members along an arced pathway, and means for temporarily locking the internal shaping members and the external shaping members in position at incremental points along the arced pathway relative to the main assembly. The rotation assemblies define a separate rotational axis for each of the sets of internal and external shaping members, which are pivoted in opposite directions during the molding procedure. In use the dynamic nasal molding device is applied to the patient with the internal shaping members inserted into the nostrils and with the external shaping members positioned bilaterally along the alar crease between the nasal and cheek units.

In an embodiment of the invention, the frame assembly comprises a pair of brace members pivotally connected such that the angle between the brace members can be adjusted, a rotation assembly comprising a stationary member and a rotating member, coaxially aligned, mounted to each brace member, an internal shaping member and external shaping member mounted to each rotating member of the rotation assembly, such that the external shaping members can be pivoted downward along an arced path. The external shaping member preferably comprises a freely turning cover member and the internal shaping member presents a convex surface and is configured with minimal volume to minimize blockage of the nasal passage for breathing. A drive recess is provided such that a tool may be used to pivot the internal and external shaping members. Preferably, teeth or ridges are provided on the rotation assemblies such that rotational movement is indexed. During the molding process, the external shaping members are pivoted downward and the separation distance between the rotation assemblies is decreased. The combination of the internal and external shaping members serve to retain the device on the patient without need for additional affixation.

In another embodiment suitable for use with bilateral cleft lip deformities, means for molding the columella-prolabial junction are provided, the means comprising an inferior dynamic molding assembly connected to the frame assembly. The inferior dynamic molding assembly comprises a threaded rod member disposed within a threaded bore, and a transverse plate member connected to the threaded rod member, wherein rotation of the threaded rod member advances the transverse plate member against the prolabium.

DETAILED DESCRIPTION OF THE INVENTION

With reference to the drawings, the dynamic nasal molding device or appliance will now be described in detail with regard for the best mode and preferred embodiment or embodiments, along with its method of use in correcting cleft lips. In general, the dynamic nasal molding device is an adjustable orthopedic appliance adapted for shaping and molding the cartilage, tissues, etc. of the nose, upper mouth, gums and upper lip of infants having unilateral or bilateral cleft lips in order to promote symmetry and proper morphology of these anatomical features prior to the corrective surgical procedures used to close the cleft. The dynamic nasal molding device is self-supporting and self-retaining on the patient, such that the need for adhesive tape or elastic members to maintain the device on the patient is obviated or greatly minimized. The dynamic nasal molding device is easily sized and oriented relative to each patient, and incremental adjustment of the device during the corrective process is easily accomplished.

The dynamic nasal molding device comprises in a most general sense a main frame assembly 10, a pair of rotation assemblies 40 connected to the frame assembly 10, a pair of intra-nasal extensions or internal shaping members 20 and a pair of extra-nasal extensions of external shaping members 30, wherein one of the internal shaping members 20 and one of the external shaping members 30 are connected to one of said rotation assemblies 40, and means for repositioning the internal shaping members 20 and external shaping members 30 along an arced pathway. The device further generally comprises means for adjusting the main assembly to adjust the lateral spread or separation distance between the rotation assemblies 40, internal shaping members 20 and external shaping members 30, and means for temporarily locking the internal shaping members 20 and the external shaping members 30 in position at incremental points along the arced pathway relative to the frame assembly 10. The rotation assemblies 40 define and comprise a separate rotational axis for each of the two sets of internal and external shaping members 20 and 30, which are pivoted in opposite directions during the molding procedure. In use the dynamic nasal molding device is applied to the patient with the internal shaping members 20 inserted into the nostrils and with the external shaping members 30 positioned bilaterally along the alar crease between the nasal and cheek units.

Figure 6:
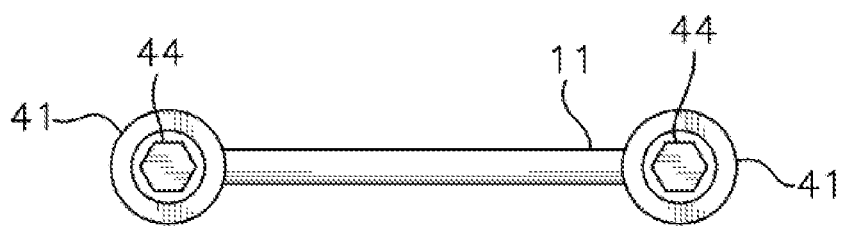
FIG. 6 is a partial view illustrating an alternative embodiment of the dynamic nasal molding device having a fixed cross bar member.
Figure 7:
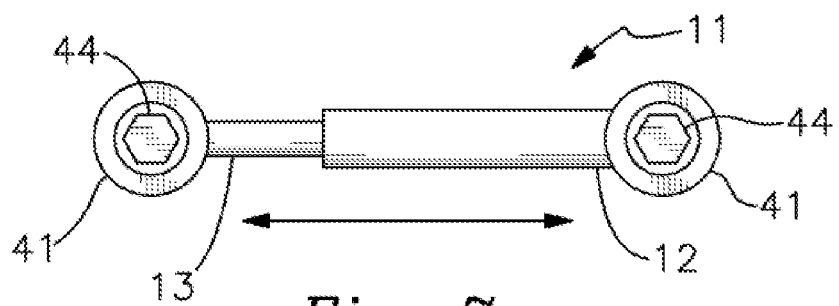
FIG. 7 is a partial view illustrating an alternative embodiment of the dynamic nasal molding device having a telescoping cross bar member.

The main frame assembly 10 in a most basic embodiment may comprise a cross bar assembly 11 of fixed length, as shown in FIG. 6, which may be replaceable with cross bar assemblies 11 of differing lengths in order to correctly space the internal shaping members 20 relative to the spacing of the patient's nostrils. If the cross bar assembly 11 is not replaceable, such as may be readily accomplished by the use of threaded connector means on the ends of the cross bar assemblies 11, different sizes of cross bar assemblies 11 may be provided in order to reduce the spread of the device as the molding process progresses. More preferably, the means for adjusting the lateral spread or separation distance between the internal shaping members 20 comprises an adjustable assembly such that the spread can be properly sized quickly and easily. In one embodiment, as shown in FIG. 7, a telescoping cross bar assembly 11 is utilized, such that the length of the cross bar assembly 11 is adjusted by extending and then contracting the sleeve 12 and shaft 13 components as the molding process progresses.

Figure 1:
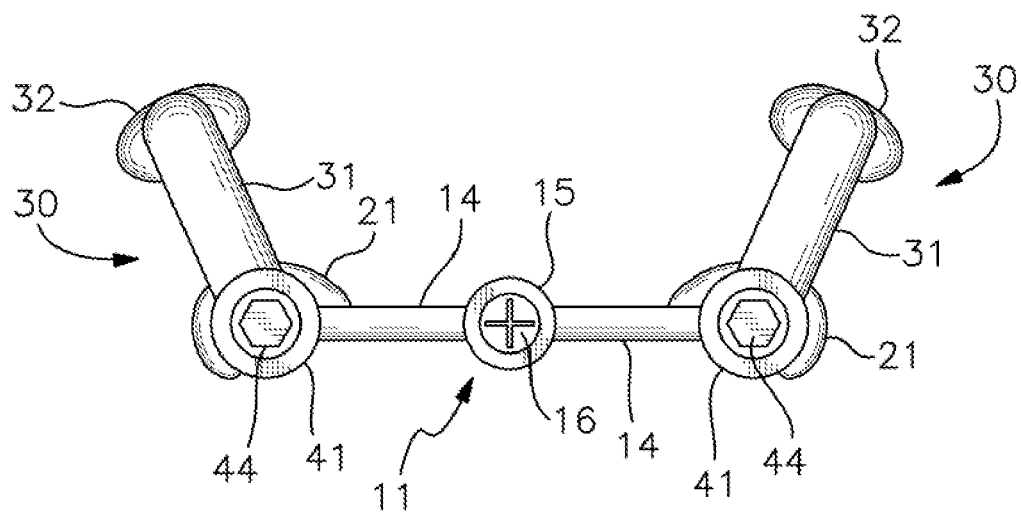
FIG. 1 is a front view of an embodiment of the dynamic nasal molding device, shown in a spread configuration representative of the configuration of the device in early stages of the molding procedure.
Figure 2:
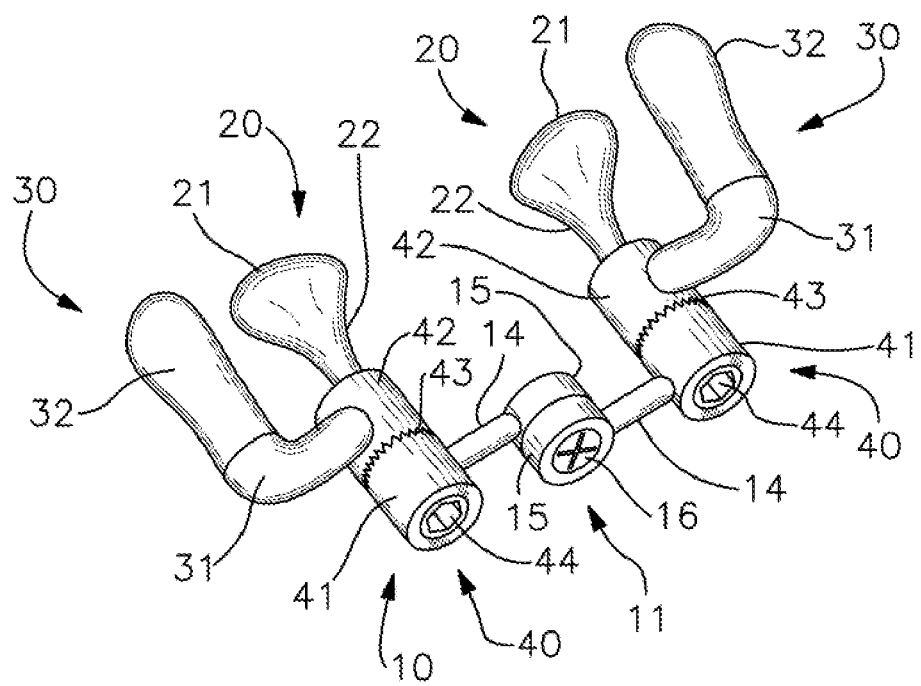
FIG. 2 is a perspective view of the embodiment of FIG. 1.
Figure 3:
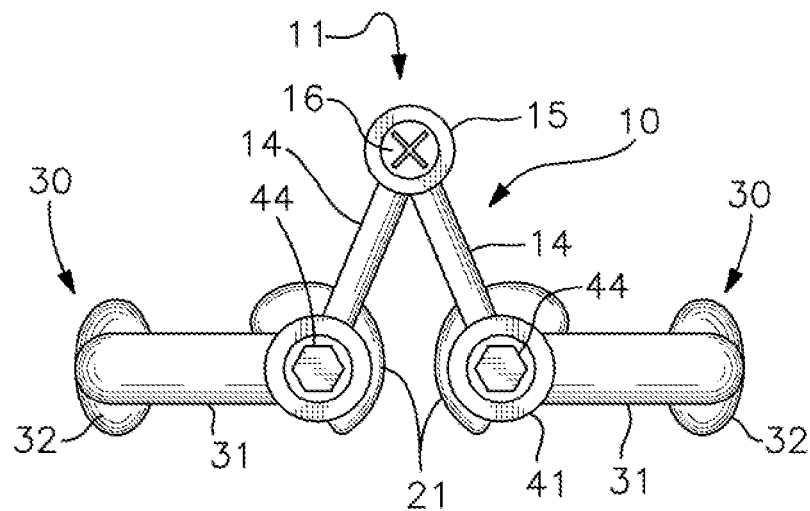
FIG. 3 is a front view of an embodiment of the dynamic nasal molding device, shown in a contracted configuration representative of the configuration of the device in the latter stages of the molding procedure.
Figure 4:
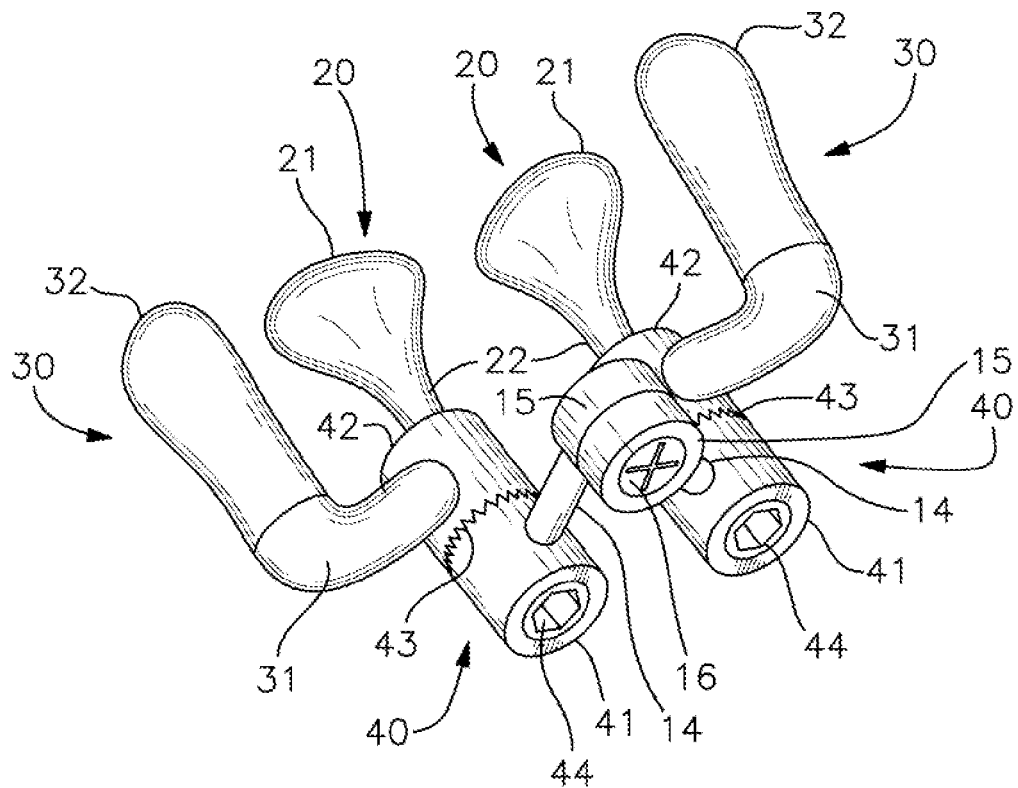
FIG. 4 is a perspective view of the embodiment of FIG. 3.

Most preferably however, the embodiment illustrated in FIGS. 1 through 5 is utilized, wherein the cross bar assembly 11 comprises a pair of brace members 14 each having a collar member 15 coaxially aligned and adapted to receive a set screw 16 or other means for securing the brace members 14 at a desired angle in known manner. With this construction, the brace members 14 may be pivoted into a parallel orientation, as shown in FIGS. 1 and 2, to maximize the separation between the internal shaping members 20, or may be pivoted to define a lesser angle, as shown in FIGS. 3 and 4, thereby bringing the internal shaping members 20 closer together, in order to size the device to match the anatomical structure presented at the beginning of the molding procedure. As the molding procedure progresses, the brace members 14 will be further pivoted to reduce the angle, thereby reducing the width of the device and the separation distance between the internal and external shaping members 20 and 30. Indexing members 43 such as teeth or ridges may be provided at the junction of collar members 15 such that the change in the angle between the brace members 14 may be more precisely controlled. Alternatively, a ratcheting drive mechanism may be utilized in place of the set screw 16 mechanism.

Figure 5:
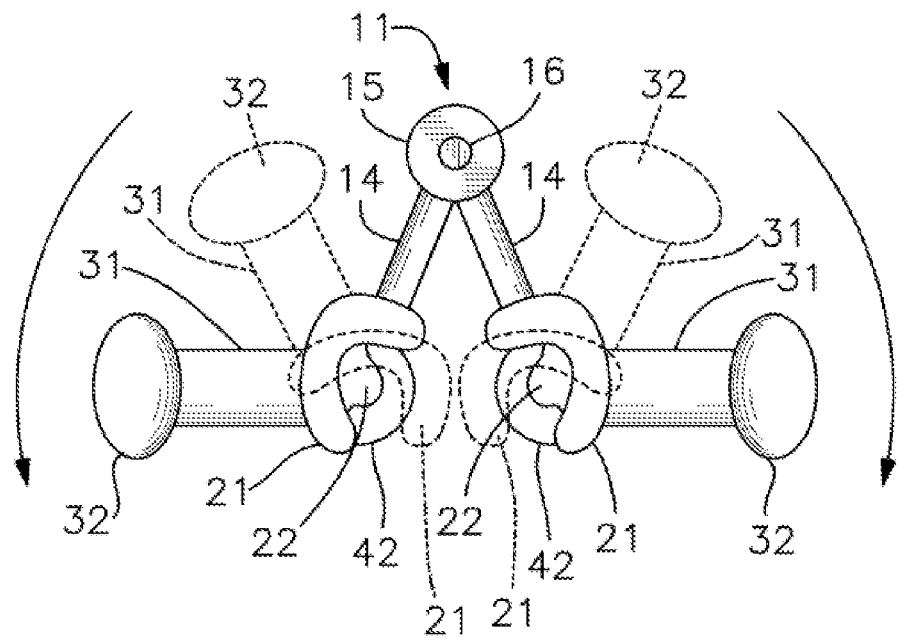
FIG. 5 is a rear view of the embodiment of FIG. 3, illustrating the repositioning of the internal and external shaping members along an arced pathway as the device is adjusted during the molding procedure.

Connected to the frame assembly 10 are a pair of rotation assemblies 40 each comprising a stationary member 41 and a rotating member 42 rotatably joined thereto in known manner whereby the stationary member 41 and the rotating member 42 are aligned to define a rotation axis about which a shaping set comprising an internal shaping member 20 and an external shaping member 30 is simultaneously pivoted. The stationary members 41 are connected to opposite ends of the cross bar assembly 11. Most preferably, the stationary member 41 and rotating member 42 are assembled such that relative rotation is incremental, such as by providing mating teeth or ridge members 43. The rotation may be structured so as to be uni-directional only, such as by providing a spring-loaded ratcheting mechanism or similar system in known manner. As an example, the rotation assemblies 40 may be constructed such that each incremental movement covers nine degrees and forty incremental steps are available. The rotation assemblies 40 are constructed such that the right external shaping member 30 (when viewed from the front) pivots from an upper position to a lower position in a clockwise direction about the rotation axis, while the left external shaping member 30 pivots from an upper position to a lower position in a counterclockwise direction about the rotation axis, as shown in FIG. 5. The combination of these elements present a representative example of the means for repositioning the external shaping members 30 along an arced pathway and the means for temporarily locking the external shaping members at incremental points along the arced pathway relative to the frame assembly 10. The rotation of rotating member 42 relative to stationary member 42 may be achieved by placing a drive member into a polygonal recess 44 within or connected to rotating member 42 that is accessible through stationary member 41. The spring loaded ratchet system would provide sufficient resistance such that each incremental movement is self-sustaining. Alternatively to the spring loaded ratchet system, a set screw or similar system could also be utilized to secure the rotating member 42 in the chosen position.

In other embodiments the invention may utilize a spring or other biasing member acting between each set of stationary and rotating members 41 and 42, as well as a spring acting between brace collar members 15. When these springs are not under load, they will maintain the device in a fully rotated and contracted position, as shown in FIG. 3. This unloaded configuration corresponds to the desired post-procedure nasal anatomy. With this embodiment, the device is activated by manually grasping both arm members 31 and loading the three springs by widening the device and raising the external shaping members 30 into the configuration shown in FIG. 1. Once the device is applied to the patient in the loaded configuration, the three springs will progressively exert forces at the three rotation points to progressively return the device to the unloaded configuration, thereby molding the nasal anatomy into the desired shape.

An internal shaping member 20 is connected to each of the rotating members 42 so as to extend rearward and into the nostril cavity when the device is applied to the patient. The internal shaping members or intra-nasal extensions 20 are adapted to have contact with the nasal lining directly on the undersurface of the lower lateral cartilages from the top of the ascending limb, along the genu to the lateral crus, but to have minimal contact with the alar rim. The internal shaping members 20 are therefore preferably shaped with a contoured or curved shaping surface 21 mounted on a post-type extension member 22. The internal shaping members 20 and the extension members 22 are sized and configured to occupy a relatively small volume within the nasal cavity so as to minimize interference with breathing. The internal shaping members 20 may be provided with a permanent or removable cover composed of a compressible or less rigid material such as a silicone or similar polymer. The covers may be of differing thicknesses or configurations to better size the internal shaping member 20 to the patient. The contoured shaping surface 21 presents a generally convex contact surface, preferably of eccentric shape that may be described as "ear-like" in cross-section, with one portion of the shaping surface 21 being only slightly curved while the other portion is more significantly curved.

The external shaping members or extra-nasal extensions 30 are connected to the rotating member 42 of the rotation assembly 40 by arm members 31. The initial positioning of the external shaping members 30 is determined by the anatomy of the patient and whether a single or bilateral deformity is presented. Each set of internal and external shaping members 20 and 30 is independently pivotable in opposite directions relative to the other. Generally, when a cleft deformity is presented the external shaping member 30 will extend generally upward or laterally relative to the rotation axis when the device is in the initial or early stage orientation during the molding procedure, and will be successively repositioned over a downward arc so as to extend generally medially and downward as the molding procedure progresses. The arms 31 of the external shaping members 30 extend generally rearward, and may be provided with a cover member 32 that may be removable or permanent and is preferably composed of a compressible or less rigid material such as a silicone or similar polymer. The cover members 32 may be of differing sizes, thicknesses or configurations to better conform the external shaping member 30 to the particular patient. Preferably, cover member 32 rotates freely upon the arm member 31 such that shear forces are avoided across the area of contact with the skin of the patient during activation of the device. The cover members 31 contact the skin of the alar crease at the lateral aspect of the nose and provide opposing contact to the lateral crus contact of the internal contoured shaping surfaces 21. This opposing contact on the extra-nasal and intra-nasal portion of the nasal ala ensures that when the simultaneous pivoting of contoured shaping surfaces 21, the arc movement of external shaping member 30 and the contraction of brace members 14 occurs, the resulting forces on the nose rotates the alar crease medially, while rotating the lateral crura upwards and laterally. Because the separation distance of the rotation assemblies 40 is progressively narrowed during the molding process, the travel arcs of the internal shaping members 20 and external shaping members 30 relative to the patient will be eccentric rather than circular. The tissue compressed between the internal and external shaping members 20 and 30 maintains the device in place on the patient without requiring additional affixation means, such as adhesive tape or the like.

In the initial or early stage orientation during the molding procedure, the contoured shaping surface 21 is disposed superiorly such that the portion that will contact the lateral crus is more horizontally oriented, and the portion that will contact the genu is generally inferior and medial as shown in FIG. 1 and in the dotted representation of FIG. 5. As the molding procedure progresses and the external shaping members 30 are pivoted along the downward arc, the internal shaping members 20 likewise rotate, as shown in FIG. 5, since they are mounted to the rotating member 42 of the rotation assembly 40. During this rotation movement, the contoured shaping surface 21 assumes a more vertical position which elevates the genu of the lower lateral cartilages, and a more medial position which coincides with the medial force applied to the alar crease skin by the arc movement of external shaping member 30. The simultaneous change in nasal morphology with activation of the device is therefore elevation of the genu of the nasal tip and medial movement of the alar crease and lateral crura, which is the desired change towards normal anatomy.

Typically, the device is applied within the first 4 months of life when cartilages are susceptible to permanent change in shape from molding forces. The articulating members are loosened and the device is applied by inserting the internal shaping members 20 into the nostrils. The width of the device is then adjusted such that the external shaping members 30 rest against the skin of the alar crease, and for the embodiment shown in FIGS. 1 through 5 this angular orientation for brace members 14 is secured by tightening set screw 16. The internal shaping members 20 and external shaping members 30 are then rotated using rotation assembly 40 until mild resistance is encountered. The initial positions for the respective sets of internal and external shaping members 20 and 30 will likely be different, especially when used in conjunction with unilateral cleft lip deformities, since the cleft lip deformity is present asymmetrically.

The device may be removed during nighttime hours, with the corrective gains of the device being maintained by use of a single horizontal medical tape across the cleft lip, directly underneath the nose. The device would then be replaced in the morning. As described above, the relative positions of the external shaping members 30 and the internal shaping members 20, along with the separation distance between the rotation assemblies 40 as controlled by narrowing the angle of the brace members 14, are progressively and incrementally adjusted over time to reshape the nasal anatomy of the patient. It is contemplated that these adjustments may be made by parents or other caregivers, with only periodic checks by a medical practitioner. When only mild manual compression across the base of the nose is required to achieve visual symmetry of the patient's nostrils, surgical correction may then be performed without further molding.

Figure 8:
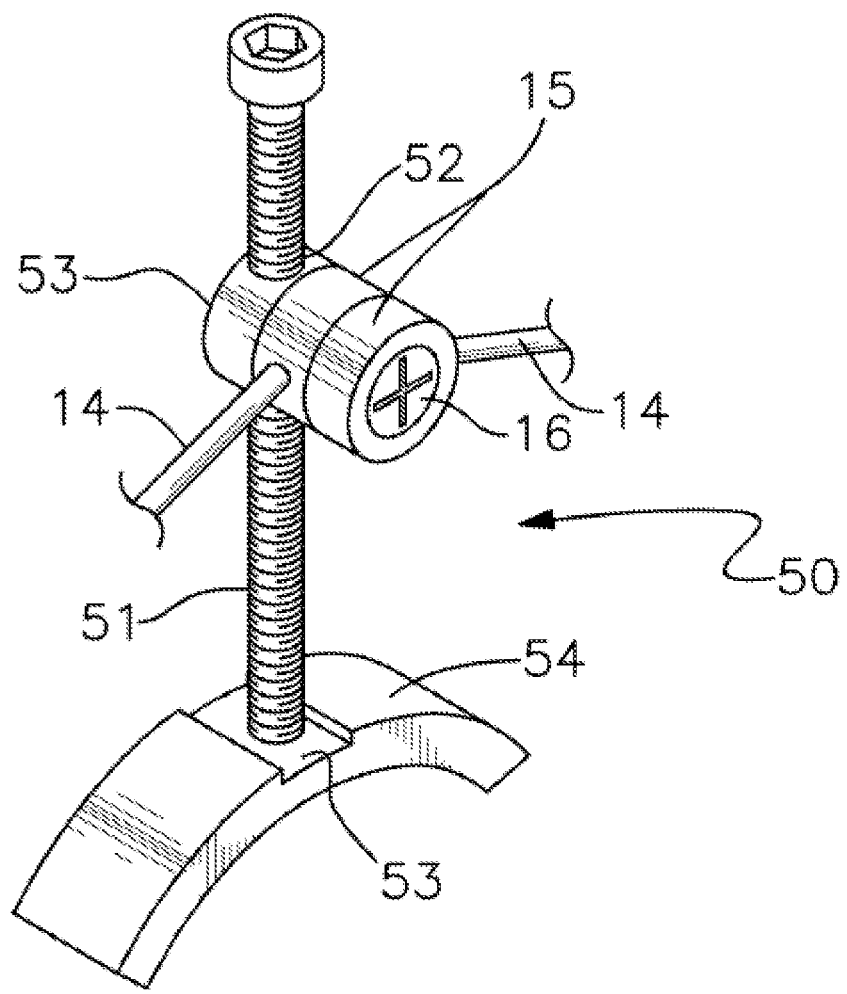
FIG. 8 is a partial view illustrating an alternative embodiment of the invention that further comprises an inferior dynamic molding assembly.

The invention as described above is designed to treat the nasal deformity associated with a unilateral cleft lip. An additional inferior molding assembly 50 is added to the invention for the treatment of nasal and prolabial deformities associated with bilateral cleft lip deformities, as shown in FIG. 8. The inferior molding assembly 50 is a means for molding the columella-prolabial junction by asserting downward pressure, and is secured to the frame assembly 10 of the device. In the representative embodiment shown, the inferior molding assembly 50 comprises a threaded rod member 51 mounted within a threaded bore 52 in attachment member 53. A curvilinear transverse plate member 54 is attached to the bottom of the vertically oriented threaded rod member 51 in a manner that allows the transverse plate member 54 to retain its orientation when said threaded rod 51 is rotated to lower the transverse plate member 54 such as by a swivel connection. A silicone or like compressible cover 55 is mounted onto the transverse plate member 54, the cover 55 conforming to the cleft anatomy at the columella-prolabial junction. To properly mold the columella-prolabial junction, threaded rod member 51 is manually rotated, thereby gradually extending the transverse plate member 54 inferiorly towards the prolabium. This exerts a downward pressure on the skin over the junction of the columella and prolabium, which lengthens the columella through the counter upward pressure on the genu of the lower lateral cartilages exerted by the internal shaping members 20. The prolabium and underlying premaxilla simultaneously experience a downward pressure that corrects the cleft lip related deformity of anterior and superior displacement of the premaxilla.

The invention, with or without the inferior molding assembly 50, can be used in conjunction with existing generic techniques of NAM, such as skin taping and the use of an intraoral molding plate for the treatment of the alveolar cleft. Existing NAM techniques use either a dynamic or passive molding plate to decrease the width of the alveolar cleft. Use of this invention will not preclude use of such molding plates, with the devices being used independently or in a connected manner.

It is contemplated that certain equivalents or substations for elements set forth above may be obvious to those of ordinary skill in the art, and therefore the true scope and definition of the invention is to be as set forth in the following claims.

I claim:

1. A method of pre-surgically molding a cleft lip deformity in a patient comprising the steps of:
    providing a dynamic nasal molding device adapted for pre-surgical molding of cleft lip deformities in a patient, said device comprising:
    a frame assembly;
    a pair of rotation assemblies connected to said frame assembly defining a pair of separate, non-overlapping, parallel rotation axes;
    a pair of intra-nasal internal shaping members and a pair of extra-nasal external shaping members, one of said internal shaping members and one of said external shaping members connected to one of said rotation assemblies, and the other of said internal shaping members and the other of said external shaping members connected to the other of said rotation assemblies, whereby said internal shaping members and said external shaping members pivot along arced pathways;
    means for adjusting the frame assembly to adjust the separation distance between said rotation assemblies;
    means for locking said internal shaping members and said external shaping members at points along said arced pathway;
    wherein said internal shaping members are adapted to be positioned in the nostrils of the patient having a cleft lip deformity and said external shaping members are adapted to be positioned along the alar creases of the patient, such that the tissue of the patient is compressed between the internal shaping members and the external shaping members so as to retain the device on the patient;
    inserting said internal shaping members into the nostrils of said patient and positioning said external shaping members along the alar creases of said patient such that tissue of said patient is between said internal shaping members and said external shaping members;
    adjusting the means for adjusting the frame assembly to change the separation distance between said rotation assemblies and pivoting said internal shaping members and said external shaping members such that mild resistance is encountered; and
    incrementally adjusting the separation distance between said rotation assemblies to narrow the distance between said rotation assemblies and incrementally pivoting said internal shaping members and said external shaping members to mold the nasal anatomy of the patient into a desired morphology.

2. The method of claim 1, wherein said providing step comprises providing a dynamic nasal molding device wherein said means for adjusting the frame assembly to adjust the separation distance between said rotation assemblies comprises a sleeve member and a shaft member.

3. The method of claim 1, wherein said providing step comprises providing a dynamic nasal molding device wherein said means for adjusting the frame assembly to adjust the separation distance between said rotation assemblies comprises a pair of brace members pivotally joined such that the angle between said brace members is adjustable.

4. The method of claim 3, wherein said providing step comprises providing a dynamic nasal molding device wherein said means for adjusting the frame assembly to adjust the separation distance between said rotation assemblies comprises a pair of coaxially aligned brace collar members retaining a set screw.

5. The method of claim 3, wherein said providing step comprises providing a dynamic nasal molding device wherein said rotation assembly each comprises a coaxially aligned stationary member and rotating member, wherein said stationary members are connected to said brace members, and wherein said internal shaping members and said external shaping members are connected to said rotating members.

6. The method of claim 5, wherein said providing step comprises providing a dynamic nasal molding device wherein said means for locking said internal shaping members and said external shaping members at points along said arced pathway comprises indexing members disposed between said stationary members and said rotating members of said rotation assemblies.

7. The method of claim 6, wherein said providing step comprises providing a dynamic nasal molding device wherein said means for locking said internal shaping members and said external shaping members at points along said arced pathway further comprises a polygonal recess connected to said rotating member that is accessible through said stationary member.

8. The method of claim 7, wherein said providing step comprises providing a dynamic nasal molding device wherein said means for adjusting the frame assembly to adjust the separation distance between said rotation assemblies comprises a pair of coaxially aligned brace collar members retaining a set screw.

9. The method of claim 8, wherein said providing step comprises providing a dynamic nasal molding device wherein each of said external shaping members comprises a removable cover.

10. The method of claim 8, wherein said providing step comprises providing a dynamic nasal molding device wherein each of said internal shaping members comprises a convexly contoured shaping surface connected to an extension member.

11. The method of claim 1, wherein said providing step comprises providing a dynamic nasal molding device wherein each of said external shaping members comprises a removable cover.

12. The method of claim 1, wherein said providing step comprises providing a dynamic nasal molding device wherein each of said internal shaping members comprises a convexly contoured shaping surface connected to an extension member.

13. The method of claim 1, wherein said providing step comprises providing a dynamic nasal molding device further comprising means for molding the columella-prolabial junction of the patient;
   said method further comprising the step of molding the columella-prolabial junction of the patient.

14. The method of claim 13, wherein said providing step comprises providing a dynamic nasal molding device wherein said means for molding the columella-prolabial junction comprises an inferior dynamic molding assembly connected to said frame assembly, said inferior dynamic molding assembly comprising a threaded rod member disposed within a threaded bore, and a transverse plate member connected to said threaded rod member, wherein rotation of said threaded rod member advances said transverse plate member.

15. The method of claim 14, wherein said step of molding the columella-prolabial junction comprises advancing said transverse plate member to press against the prolabium of the patient; and incrementally advancing said transverse plate member against said prolabium.

16. A method of pre-surgically molding a cleft lip deformity in a patient comprising the steps of:
   providing a dynamic nasal molding device comprising: an adjustable frame assembly comprising a pair of brace members pivotally joined such that the angle between said brace members is adjustable; a pair of rotation assemblies, one of said rotation assemblies connected to one of said brace members of said frame assembly, and the other of said rotation assemblies connected to the other of said brace members of said frame assembly, said rotation assemblies each comprising a coaxially aligned stationary member and rotating member, wherein said stationary members are connected to said brace members; said pair of rotation assemblies defining a parallel pair of rotation axes; and a pair of intra-nasal internal shaping members and a pair of extra-nasal external shaping members, one of said internal shaping members and one of said external shaping members connected to said rotating member of one of said rotation assemblies, and the other of said internal shaping members and the other of said external shaping members connected to said rotating member of the other of said rotation assemblies, whereby said internal shaping members and said external shaping members pivot along arced pathways upon rotation of said rotating members;
   inserting said internal shaping members into the nostrils of said patient and positioning said external shaping members along the alar creases of said patient such that tissue of said patient is between said internal shaping members and said external shaping members;
   adjusting the angle of said brace members and pivoting said internal shaping members and said external shaping members such that mild resistance is encountered; and
   incrementally adjusting said angle of said brace members to narrow the distance between said rotation assemblies and incrementally pivoting said internal shaping members and said external shaping members to mold the nasal anatomy of the patient into a desired morphology.

17. The method of claim 16, wherein said providing step comprises providing a dynamic nasal molding device comprising indexing members positioned between said stationary member and said rotating member of each of said rotation assemblies.

18. The method of claim 16, wherein said providing step comprises providing a dynamic nasal molding device wherein said internal shaping members each comprise a convexly contoured shaping surface mounted onto an extension member.

19. The method of claim 16, further comprising the steps of:
   providing an inferior dynamic molding assembly connected to said frame assembly, said inferior dynamic molding assembly comprising a threaded rod member disposed within a threaded bore, and a transverse plate member connected to said threaded rod member, wherein rotation of said threaded rod member advances said transverse plate member;
   advancing said transverse plate member to press against the prolabium of the patient; and
   incrementally advancing said transverse plate member against said prolabium.

* * * * *